United States Patent [19]
Nita et al.

[11] Patent Number: 5,312,328
[45] Date of Patent: May 17, 1994

[54] ULTRA-SOUND CATHETER FOR REMOVING OBSTRUCTIONS FROM TUBULAR ANATOMICAL STRUCTURES SUCH AS BLOOD VESSELS

[75] Inventors: Henry Nita, Lake Forest; Douglas H. Gesswein, Mission Viejo; James D. Passafaro, Santa Ana, all of Calif.

[73] Assignee: Baxter International Inc., Deerfield, Ill.

[21] Appl. No.: 911,546

[22] Filed: Jul. 9, 1992

Related U.S. Application Data

[63] Continuation-in-part of Ser. No. 878,795, May 5, 1992, Pat. No. 5,267,954, which is a continuation-in-part of Ser. No. 787,292, Nov. 4, 1991, abandoned, which is a continuation-in-part of Ser. No. 640,190, Jan. 11, 1991, Pat. No. 5,364,115.

[51] Int. Cl.⁵ .............................................. A61B 17/20
[52] U.S. Cl. ...................................... 604/22; 606/169; 601/2
[58] Field of Search ............. 128/24 AA; 604/21, 22, 604/52; 606/159, 169–171

[56] References Cited

U.S. PATENT DOCUMENTS

| | | | |
|---|---|---|---|
| 3,352,303 | 11/1967 | Delaney | 604/22 |
| 3,526,219 | 9/1970 | Balamuth | 606/169 |
| 3,565,062 | 2/1971 | Kuris | 128/24 AA |
| 3,823,717 | 7/1974 | Pohlman et al. | 128/24 AA |
| 3,861,391 | 1/1975 | Antonevich et al. | 128/24 AA |
| 3,896,811 | 7/1975 | Storz | 128/24 AA |
| 4,692,139 | 9/1987 | Stiles | 604/22 |
| 4,808,153 | 2/1989 | Parisi | 604/22 |
| 4,870,953 | 10/1989 | Don Micheal et al. | 604/22 |
| 4,920,954 | 5/1990 | Alliger et al. | 128/24 AA |
| 4,924,863 | 5/1990 | Sterzer | 606/27 |
| 4,936,281 | 6/1990 | Stasz | 606/48 |
| 5,195,955 | 3/1993 | Don Michael | 604/22 |
| 5,248,296 | 9/1993 | Alliger | 128/24 AA |

FOREIGN PATENT DOCUMENTS 0316796  5/1989  European Pat. Off. ....... 128/24 AA Primary Examiner—John D. Yasko
Assistant Examiner—Michael Rafa
Attorney, Agent, or Firm—Stetina & Brunda

[57] ABSTRACT

An ultrasound catheter for removing obstructions from tubular anatomic structures such as blood vessels, said catheter comprising an elongate flexible catheter body having an ultrasound transmission member or wire extending longitudinally therethrough. A distal head is formed on the distal end of the ultrasound transmission member or wire and is affixed to the catheter body. The ultrasound transmission member or wire may be formed of any material capable of transmitting ultrasonic energy including various superelastic metal alloys such as nickel titanium metal alloys. The distal portion of the ultrasound transmission member or wire may be of reduced diameter to provide enhanced flexibility and/or amplification of the ultrasonic energy through the distal portion of the ultrasound transmission member or wire. A proximal end connector may be provided with a sonic connector to effectively couple the catheter to the ultrasound transducer.

14 Claims, 7 Drawing Sheets

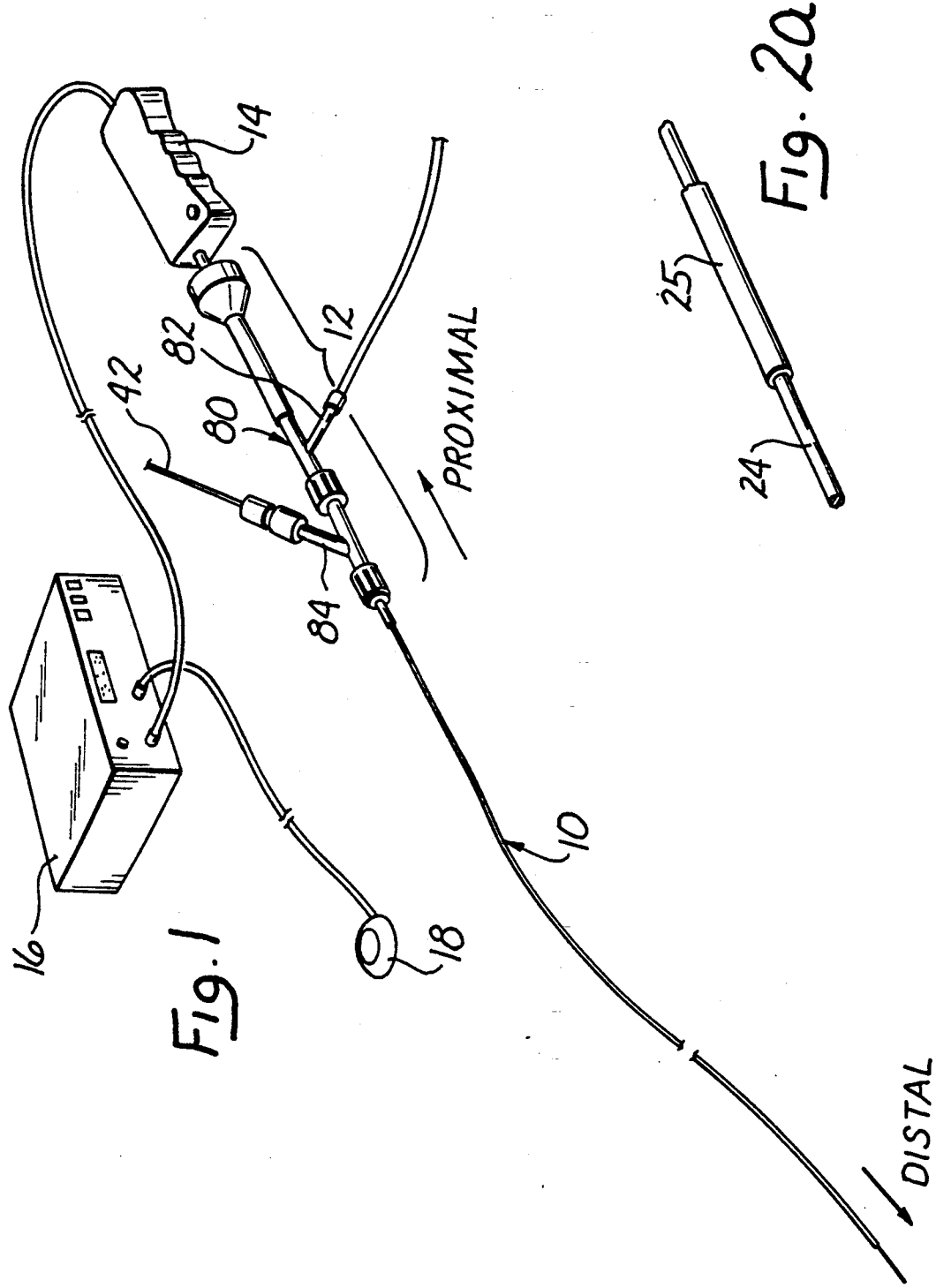

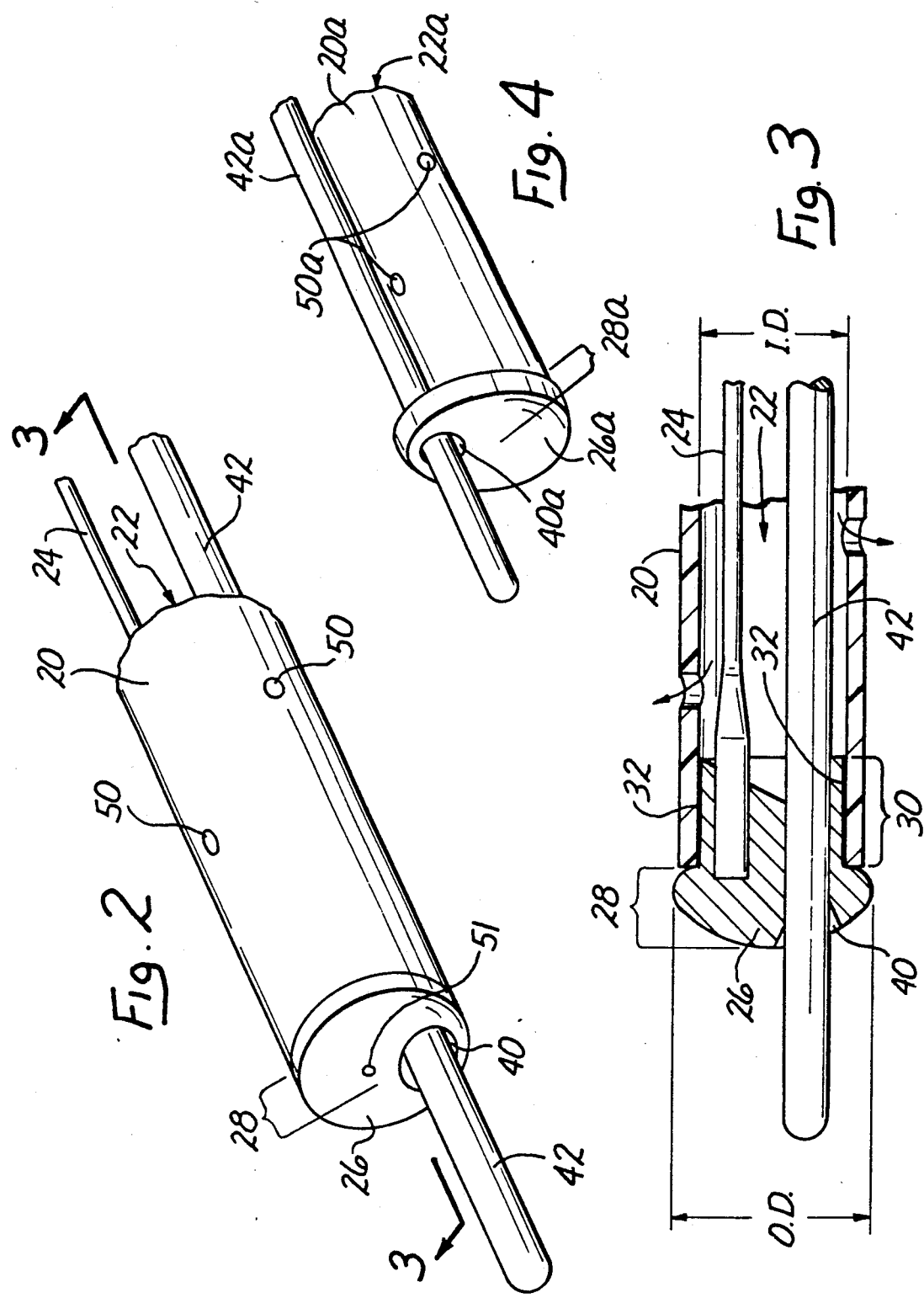

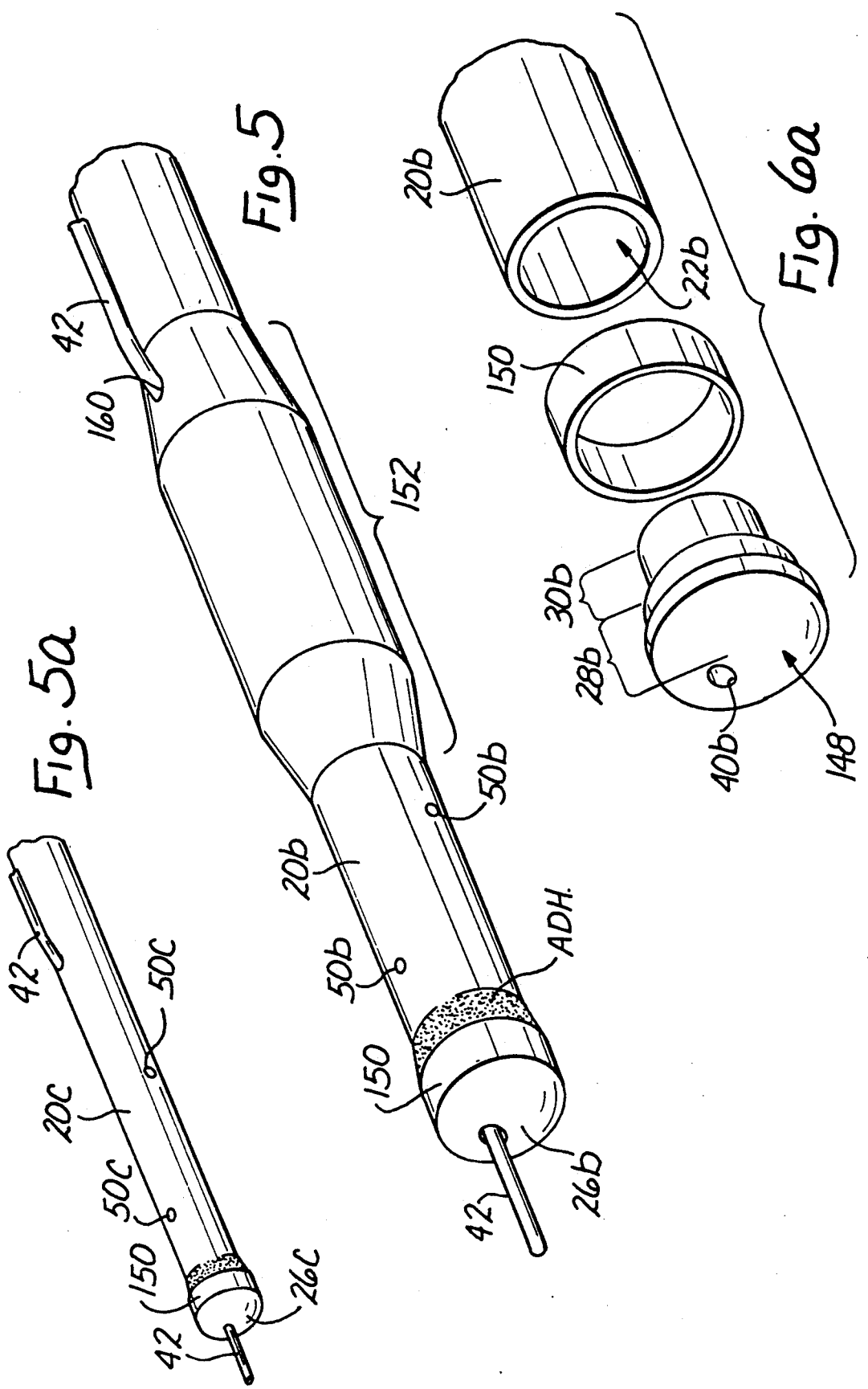

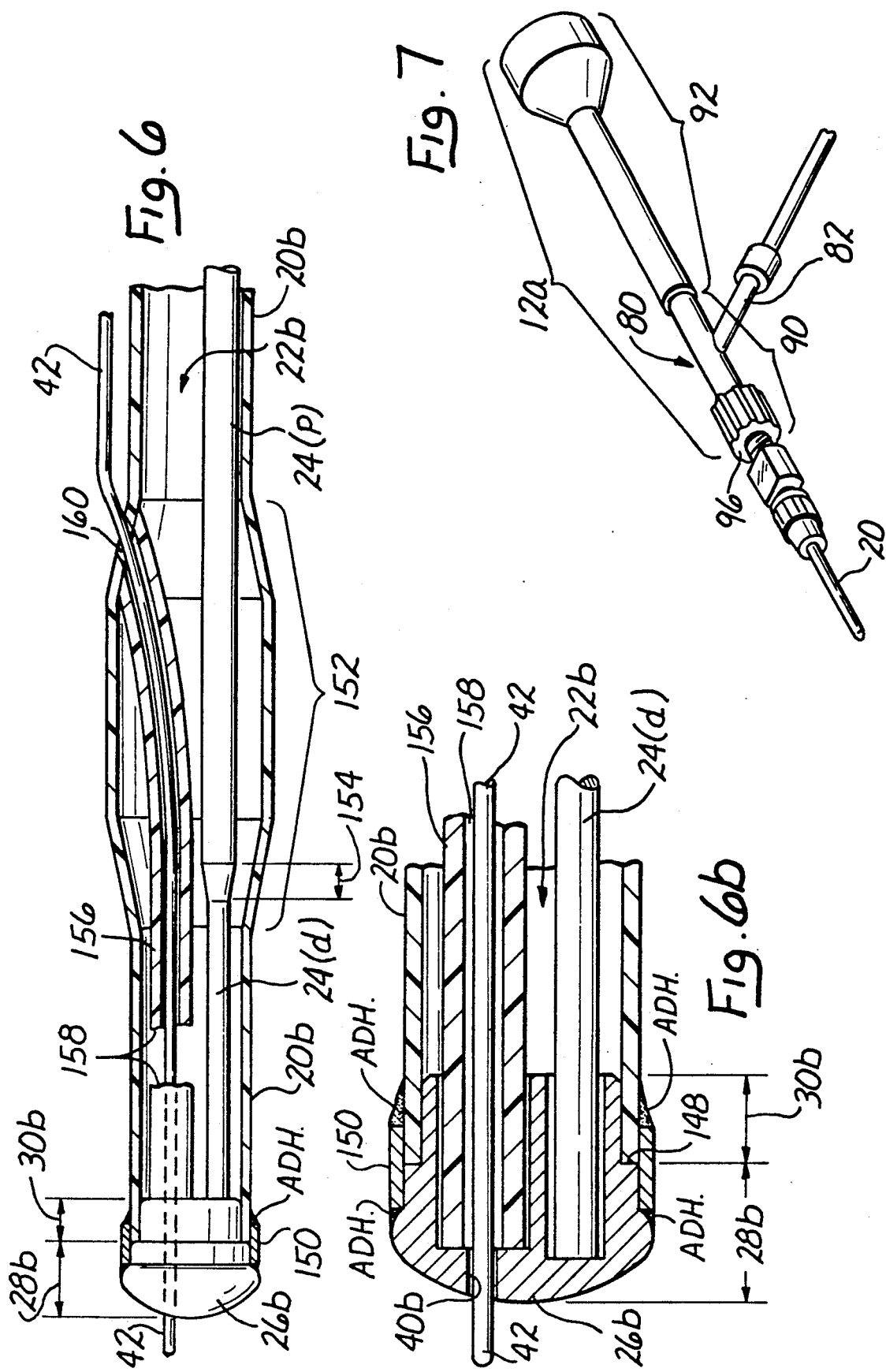

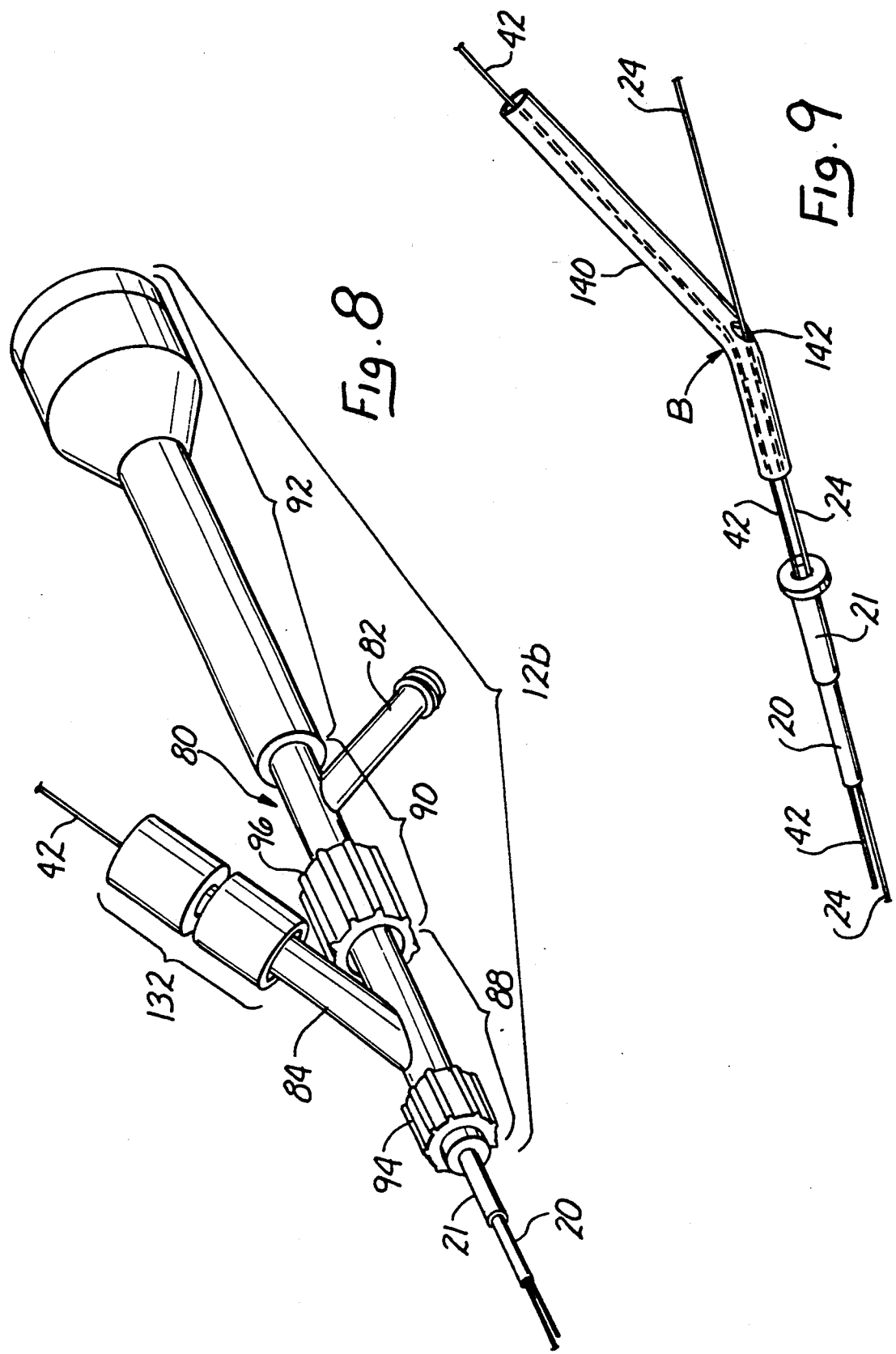

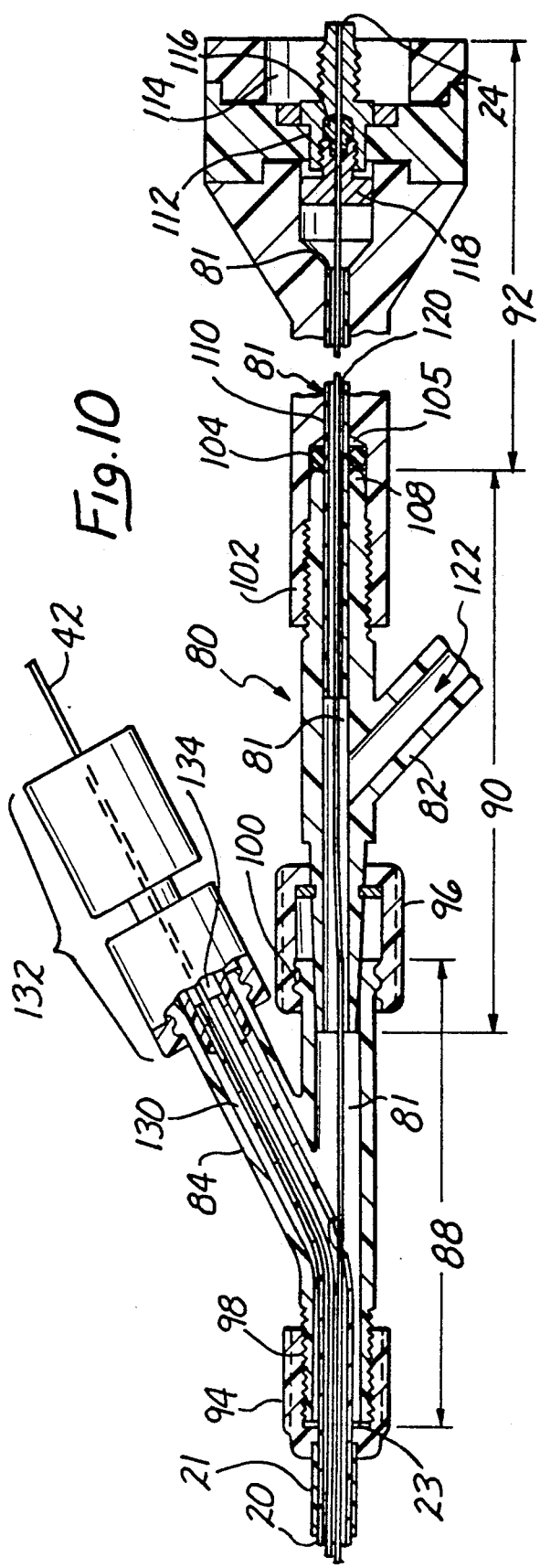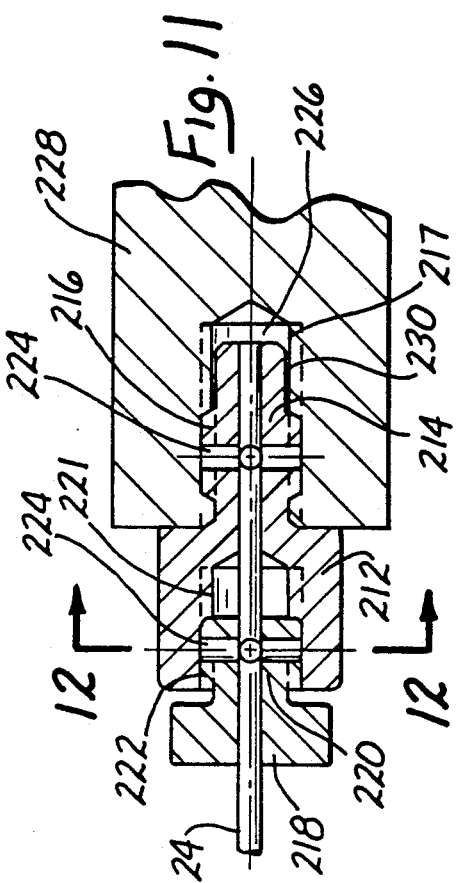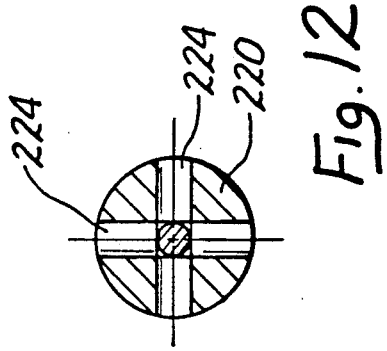

ULTRA-SOUND CATHETER FOR REMOVING OBSTRUCTIONS FROM TUBULAR ANATOMICAL STRUCTURES SUCH AS BLOOD VESSELS

This application is a continuation-in-part of U.S. application Ser. No. 07/878,795, filed on May 5, 1992, now U.S. Pat. No. 5,267,954 which is a continuation-in-part of U.S. application Ser. No. 07/787,292, filed Nov. 4, 1991 abandoned, which is a continuation-in-part of U.S. application Ser. No. 07/640,190, filed Jan. 11, 1991 now U.S. Pat. No. 5,304,115.

FIELD OF THE INVENTION

The present invention pertains to medical equipment and more particularly an ultrasonic catheter for ablating obstructions within tubular anatomical structures such as blood vessels.

BACKGROUND OF THE INVENTION

A number of ultrasonic devices have heretofore been proposed for use in ablating or removing obstructive material from blood vessels. Examples of ultrasonic ablation devices in related apparatus purported to be useable in removing obstructions from blood vessels include those described in U.S. Pat. Nos. 3,433,226 (Boyd), 3,823,717 (Pohlman, et al.), 4,808,153 (Parisi), 4,936,281 (Stasz), 3,565,062 (Kuris), 4,924,863 (Sterzer), 4,870,953 (Don Michael, et al., and 4,920,954 (Alliger, et al.), as well as other patent publications WO87-05739 (Cooper), WO89-06515 (Bernstein, et al.), WO90-0130 (Sonic Needle Corp. ), EP316789 (Don Michael, et al.), DE3,821,836 (Schubert) and DE2,438,648 (Pohlman).

Ultrasound transmitting catheters have been utilized to successfully ablate various types of obstructions from blood vessels of humans and animals. Particular success has been observed in ablation of atherosclerotic plaque or thromboembolic obstructions from peripheral blood vessels such as the femoral arteries. Successful applications of ultrasonic energy to smaller blood vessels, such as the coronary arteries, necessitates the use of ultrasound transmitting catheters which are sufficiently small and flexible to permit transluminal advancement of such catheter through the tortuous vasculature of the aortic arch and coronary tree. Accordingly, the safety and efficacy of removing obstructions from coronary arteries by way of ultrasound is largely dependent upon the size and flexibility of the ultrasound transmitting catheter(s) employed.

Thus, there exists a need in the art for improved ultrasound catheters which are sufficiently flexible to be advanced and inserted into both small tortuous blood vessels, such as the coronaries arteries.

SUMMARY OF THE INVENTION

In accordance with the invention, there is provided an ultrasound catheter device comprising an elongate flexible catheter body having at least one lumen extending longitudinally therethrough. An elongate ultrasound transmission member extends through the catheter body and is connected, at its distal end, to a distal head. The entire distal head, or a portion thereof, may protrude out of and beyond the distal end of the catheter body. The distal head is secured or affixed to the catheter body.

Further in accordance with the invention, there is provided an ultrasound catheter having an elongate ultrasound transmission member extending longitudinally therethrough, said ultrasound transmission member being formed of one or more superelastic materials, such as certain superelastic metal alloys, which exhibit superelastic properties within the range of temperatures undergone by the ultrasound transmission member during operation of the device. Still further in accordance with the invention, there is provided an ultrasound catheter having an elongate ultrasound transmission member extending longitudinally therethrough, said elongate ultrasound transmission member having a proximal portion of a first cross-sectional dimension or diameter and a distal portion of a second cross-sectional dimension or diameter less than said first cross-sectional dimension or diameter. Such lessening of the cross-sectional dimension or diameter of the distal portion of the ultrasound transmission member results in more flexibility and less rigidity of the ultrasound transmission member within such region thereof. Additionally, such lessening of the cross-sectional dimension or diameter of the distal portion of the ultrasound transmission member results in an amplification of ultrasound transmitted through such transmission member.

Still further in accordance with the invention, there is provided an ultrasound transmission catheter having an elongate ultrasound transmission member extending therethrough and a guidewire passage lumen extending longitudinally through the catheter to permit the catheter to be utilized in accordance with over-the-wire (OTW) insertion techniques.

Still further in accordance with the invention, there is provided an ultrasound transmission catheter having an elongate ultrasound transmitting member extending longitudinally therethrough and a guidewire guide or member extending laterally outboard of the catheter in at least one position thereon. Such guidewire guide or support member is provided with at least one guidewire passage aperture extending longitudinally therethrough to permit a guidewire to be passed therethrough, thereby permitting the ultrasound catheter to be utilized in accordance with monorail guidewire insertion techniques.

Still further in accordance with the invention, there is provided an ultrasound transmission catheter having an elongate ultrasound transmitting member extending longitudinally therethrough and a distal guidewire lumen extending longitudinally through only a distal portion of the catheter. Such distal guidewire passage lumen comprises an elongate tube or passageway having a distal end and a proximal end. The distal end of the elongate tube or passageway opens through a distal end aperture and the proximal end of the elongate tube or passageway opens through a guidewire entry/re-entry aperture formed at a point in the sidewall of the catheter. Accordingly, a guidewire may be proximally or distally advanced through said distal guidewire lumen within the distal portion of the catheter body while a remaining proximal portion of the guidewire resides outside of and next to the catheter body.

Still further in accordance with the invention, there are provided proximal end connector assemblies which operate to connect the proximal end of an ultrasound transmission catheter to an ultrasound transducer. The proximal end connector assemblies of the present invention comprise generally tubular members having at least one longitudinal bore through which the ultrasound transmission member of the catheter may extend and at least one connector apparatus for connecting the ultrasound transmission member to an attendant ultrasound transducer. In one embodiment, the sonic connector comprises a compressible gripping ferrule which may be tightened to grip and firmly hold the ultrasound transmission member in place to provide a damping effect to prevent undesirable transverse movement. In a second embodiment, the sonic connector comprises a plurality of compressible plugs which are also tightened to grip and firmly hold the ultrasound transmission member to achieve the required damping effect, as well as to secure the ultrasound transmission member to the sonic connector. In a third embodiment, the sonic connector comprises both a plurality of compressible plugs and a gripping ferrule. In other further embodiments, a polymeric coating may be applied to the various connections between the ultrasound transmission member and the sonic connector, either in conjunction with the gripping ferrule and/or the compressible plugs or independent of the ferrule and plugs, to secure these connections.

The proximal end connector assemblies of the present invention may be provided with one or more fluid infusion sidearms for infusing coolant liquid or other fluid through the bore of the proximal connector and through a lumen of the catheter body. Additionally, in some embodiments, a guidewire passage sidearm may be positioned on the proximal connector assembly to permit insertion and/or extraction of a guidewire through the proximal connector assembly and through the body of the catheter. One or more guidewire diverting members, such as an angled tubular member, may be positioned within the proximal connector assembly to divert a proximally advancing guidewire out of a guidewire sidearm positioned thereon.

Still further in accordance with the invention, there is provided an ultrasound catheter having an elongate ultrasound transmission member extending longitudinally therethrough, said ultrasound transmission member having a friction-reducing coating or outer jacket formed thereon. Such friction reducing coating or outer jacket may comprise a layer of low friction polymeric material such as polytetrafluoroethylene (ptfe) (teflon ™ Dupont, Inc., Wilmington, Delaware) or polyethylene. Such friction reducing coating or jacket may be disposed over the entire outer surface of the ultrasound transmission member or may be confined to a specific region or regions thereof.

Further objects and aspects of the invention will become apparent to those skilled in the art upon reading and understanding the following detailed description and the accompanying drawings.

BRIEF DESCRIPTIONS OF THE DRAWINGS

FIG. 1 is a perspective view of a first embodiment of an over-the-wire ultrasound catheter of the present invention.

FIG. 2 is partial enlarged perspective view of the distal end of a first embodiment of an over-the-wire ultrasound catheter of the present invention.

FIG. 2a is a partial cut-away perspective view of an ultrasound transmission member positionable in an ultrasound catheter and having a friction reducing coating or jacket disposed thereon.

FIG. 3 is a longitudinal sectional view through Line 3-3 of FIG. 2.

FIG. 4 is an enlarged perspective view of the distal portion of an embodiment of a monorail ultrasound catheter of the present invention.

FIG. 5 is a perspective view of the distal portion of an embodiment of an ultrasound catheter of the present invention having a region of enlarged diameter and a partial guidewire lumen running through a distal portion of the catheter body.

FIG. 5a is a perspective view of the distal portion of an embodiment of an ultrasound catheter of the present invention having a partial guidewire lumen running through a distal portion of the catheter body.

FIG. 6 is a longitudinal sectional view of the embodiment of the ultrasound catheter shown in FIG. 5.

FIG. 6a is an exploded view of a distal tip of the ultrasound catheter embodiments shown in FIGS. 5 and 5a.

FIG. 6b is an enlarged view of the distal end of the longitudinal sectional view of FIG. 6.

FIG. 7 is a perspective view of a proximal end connector end apparatus positionable on the proximal end of an ultrasound catheter of the present invention for connecting the catheter to an ultrasound transducer.

FIG. 8 is a perspective view of an alternative proximal end connector assembly positionable on the proximal end of an ultrasound catheter having an internal guidewire lumen for attaching the ultrasound catheter to an ultrasound transducer.

FIG. 9 is a longitudinal sectional view of the proximal end connector assembly shown in FIG. 5.

FIG. 10 is a perspective view of the guidewire diverter apparatus and a first embodiment of a sonic connector positioned within the proximal end connector assembly shown in FIGS. 5 and 6.

FIG. 11 is an enlarged perspective view of a second embodiment of a sonic connector positioned within the proximal end connector assembly of FIG. 10.

FIG. 12 is a cross-sectional view of the sonic connector of FIG. 11 taken along Line 12—12 in FIG. 11.

DETAILED DESCRIPTION OF PREFERRED EMBODIMENTS

Figure 13:
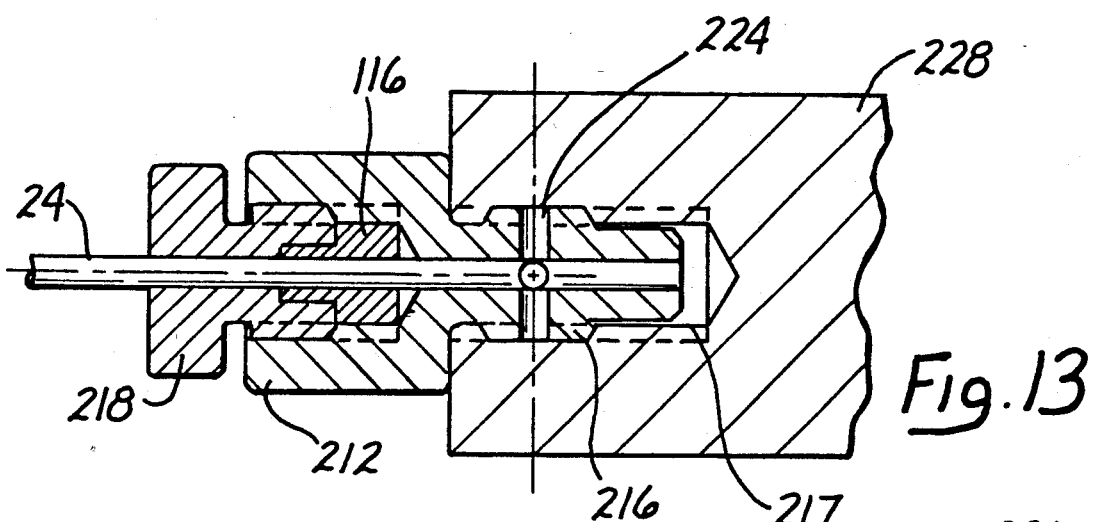
FIG. 13 is an enlarged perspective view of a third embodiment of a sonic connector positioned within the proximal end connector assembly of FIG. 10.

The following detailed description in the accompanying drawings are provided for purposes of illustrating and describing specific embodiments of the present invention and are not intended to limit the scope of the present invention in any way.

The ultrasound catheters of the present invention include both "over-the-wire" configurations and "monorail" configuration. As used herein, the term "over-the-wire" shall refer to an ultrasound catheter which has a guidewire passage lumen formed within the body of the catheter such that a flexible guidewire may be advanced through the body of the catheter and out of a guidewire passage aperture formed in the distal end of the catheter. As used herein, the term "monorail" shall refer to an ultrasound catheter which has a guidewire supporting structure at or near the distal tip of the catheter and extending laterally outboard of the outer surface of the catheter body such that a flexible guidewire may reside next to the catheter body with the distal end of such guidewire extending through and/or being held by the guidewire supporting structure formed on or near the distal end of the catheter body.

FIG. 1 is a perspective showing of an over-the-wire ultrasound catheter 10 of the present invention having a proximal end connector assembly 12 mounted on the proximal end thereof. An ultrasound transducer 14 is connected to the proximal end of the proximal connector assembly 12. An ultrasound generator 16 having a foot actuated on/off switch 18 is operatively connected to the ultrasound generator 14 so as to send ultrasonic energy through the ultrasound catheter 10, when desired.

One embodiment of an over-the-wire ultrasound catheter 10 of the present invention are shown in FIGS. 2 and 3. As shown, one embodiment of an over-the-wire ultrasound catheter 10 of the present invention comprises a flexible tubular catheter body 20 having a hollow lumen 22 extending longitudinally therethrough. This over-the-wire catheter body preferably has an outside diameter of 0.5 mm–5.0 mm. In catheters 10 intended for insertion into tortuous or relatively small anatomical structures (e.g., the coronary arteries) it is preferable that the outer diameter of the catheter body 20 be 0.25 mm–2.5 min.

One embodiment of a monorail ultrasound catheter 10a of the present invention are shown in FIG. 4. As shown, a monorail ultrasound catheter 10a of the present invention comprises a flexible tubular catheter body 20a having a hollow lumen 22a extending longitudinally therethrough. As with the over-the-wire catheter 10, it is preferable that the outside diameter of the catheter body 20a of the monorail catheter 10a be 0.5 mm–5.0 mm. In monorail catheters 10a intended for use in tortuous or relatively small anatomical structures (e.g., the coronary arteries) it is preferable that the outer diameter of the catheter body be 0.25 mm–2.0 mm and it is further specifically preferable that the width of the distal head 26a be, at its widest point, no greater than 3.0 mm such that the entire distal head 26a and the catheter body 20a may be inserted into an anatomical passageway of approximately 3.0 mm diameter, (e.g. the coronary artery).

In both the "over-the-wire" and "monorail" embodiments of the invention, an ultrasound transmission member 24 or wave guide extends longitudinally through the lumen 22 of the catheter body 20 to transmit ultrasonic energy from an ultrasound transducer 14 connected to the proximal end of the catheter 10 to the distal end thereof. Preferably a distal head 26 is mounted on the distal end of the ultrasound transmission member 24. In the embodiments shown, the distal head 26 comprises generally round, conical, or disc-shaped distal portion 28 and a reduced diameter neck or proximal portion 30. The outer diameter OD of the proximal portion 30 of the distal head 26 is approximately the same as or slightly less than the inner diameter ID of the catheter lumen 22 such that the proximal portion 30 of the distal head 26 may be inserted into the distal end of the lumen 22, to a point where the distal tip of the catheter body 20 abuts against the proximal aspect of the distal portion 28 of the distal head 26, as shown.

The ultrasound transmission member 24 may be formed of any material capable of effectively transmitting the ultrasonic energy from the ultrasound transducer 14 to the distal end of the catheter body 20, including but not necessary limited to metal, plastic, hard rubber, ceramic and/or composites thereof.

In accordance with one aspect of the invention, all or a portion of the ultrasound transmission member 24 may be formed of one or more materials which exhibit superelasticity. Such material(s) should preferably exhibit superelasticity consistently within the range of temperatures normally encountered by the ultrasound transmission member 24 during operation of the device 10.

Specifically, all or part of the ultrasound transmission member 24 may be formed of one or more metal alloys known as "shape memory alloys".

Examples of super elastic metal alloys which are usable to form the ultrasound transmission member 24 of the present invention are described in detail in U.S. Pat. Nos. 4,665,906 (Jervis); 4,565,589 (Harrison); 4,505,767 (Quin); and 4,337,090 (Harrison). The disclosures of U.S. Pat. Nos. 4,665,906; 4,565,589; 4,505,767; and 4,337,090 are expressly incorporated herein by reference insofar as they describe the compositions properties, chemistries and behavior of specific metal alloys which are superelastic within the temperature range at which the ultrasound transmission member of the present invention operates, any and all of which superelastic metal alloys may be usable to form the superelastic ultrasound transmission member 24 of the present invention.

In particular, one presently preferred superelastic metal alloy of which the ultrasound transmission member 24 may be formed is a nickel-titanium alloy wire made up of 55.8 weight percent nickel (NiTi containing 55.8% weight % Ni balance Ti). Such material is commercially available as Tinel ™ Wire from Raychem Corporation, Menlo Park, Calif.

In any embodiment of the device, the ultrasound transmission member 24 may be tapered, narrowed or otherwise reduced in cross-sectional dimension within a distal portion of the catheter so as to decrease the rigidity of the ultrasound transmission member 24 within such distal portion of the device and also to cause amplification of the ultrasound transmitted to the distal head 26. As shown in FIG. 6, such tapering or narrowing of the ultrasound transmission member divides the ultrasound transmission member into a proximal portion 24p and a distal portion 24d. An angular tapered or narrowing region 154 embodies the transition zone between the larger proximal portion 24p and the smaller distal portion 24d. Because the distal portion 24d of the ultrasound transmission member is of smaller cross-sectional diameter and less mass, it is more flexible and less rigid than the proximal portion 24p thereof. Such configuration of the ultrasound member 24 enables the relatively large sized proximal portion 24p to transmit more ultrasonic energy than if the entire length of the ultrasound transmission member 24 were to be of the relatively small cross-sectional size of the distal portion 24d thereof. Additionally, such decrease in the cross-sectional size of the distal portion 24d of the ultrasound transmission member 24 results in an amplification of the ultrasound transmitted through such distal portion 24d thereof. Thus, by limiting the reduced size portion of the ultrasound transmission member 24 to a discrete region thereof near the distal tip of the catheter, the proximal portion 24p of the ultrasound transmission member is rendered capable of transmitting a greater amount of ultrasonic energy to the distal end of the catheter than would otherwise be possible, while the reduced cross-sectional size of the distal portion of the ultrasound transmission member 24 additionally serves to amplify the ultrasound reaching the distal head 26 of the device.

In embodiments of the device wherein an enlarged region 152 is formed on the catheter body 20b, it is desirable that the taper 154 of the ultrasound transmission member 24b be positioned at the distal end of the bulge or enlarged region 152 so as to result in that portion of the catheter lying distal to the distal end of the enlarged region 152 being more flexible and less rigid than the remainder of said catheter, due to the decreased diameter of the ultrasound transmission member 24d extending through such portion.

In embodiments of the device wherein the cross-sectional dimension or outer diameter of the catheter body is substantially constant (i.e., FIG. 5a) the tapered region 154 of the ultrasound transmission member 24 may be formed at any point desired such that portion of the catheter lying distal to the tapered region 154 will, as a result, exhibit less rigidity and greater flexibility than the remainder of the catheter body.

The present invention further includes an optional improvement to the ultrasound transmission member 24 of any ultrasound transmitting catheter, said improvement comprising the disposition of a low friction coating or jacket 25 on the outer surface of all or a portion of the ultrasound transmission member 24. As shown in FIG. 2a, the low friction coating or jacket 25 may be disposed on the outer surface of the ultrasound transmission member 24 so as to completely cover the ultrasound transmission member 24 along its entire length, or along a discrete region or regions thereof. Such coating or jacket 25 may comprise a layer of low friction polymer material such as polytetrafluoroethylene (ptfe) (teflon TM Dupont, Inc., Wilmington, Del.) or other plastic materials such as polyethylene. The coating or jacket 25 may be applied as a liquid and subsequently allowed to cure or harden on the surface of the ultrasound transmission member 24. Alternatively, the coating jacket 25 may be in the form of an elongate tube slideably disposable over the outer surface of the ultrasound transmission member 24. Such coating or jacket 25 serves to prevent or diminish friction between the outer surface of the ultrasound transmission member 24 and the adjacent structures of the catheter 10 or proximal end connector assembly 12 through which the ultrasound transmission member 24 extends.

The distal head 26 is firmly bonded, attached, or connected to the catheter body 20 such that the distal head is prevented from undergoing longitudinal or transverse movement separate from or relative to the catheter body. Such non-moveable affixation of the distal head 26 to the catheter body prevents longitudinal or transverse movement of the distal head 26 apart from the catheter body 20. Additionally, such affixation of the distal head to the catheter body increases the conveyance of ultrasound energy into the distal portion of the catheter body 20, thereby resulting in enhanced cavitation effects created by the distal portion of the catheter body. Such bonding connection or attachment of the distal head 26 to the catheter body 20 may be accomplished by any suitable means. One means of attaching the distal head 26 to the catheter body 20 is through the use of adhesive 32.

In the embodiments shown in FIGS. 2–4, the adhesive 32 is applied to the proximal portion 30 of the distal head 26 prior to insertion thereof into the distal end of the lumen 22 of the catheter body 20. The adhesive 32 may comprise any suitable adhesive, such as cyanoacrylate (e.g. Loctite TM, Loctite Corp., Ontario, CANADA or Dron Alpha TM, Borden, Inc., Columbus, Ohio) or polyurethane (e.g. Dymax TM, Dymax Engineering Adhesive, Torrington, CT.) to firmly bond and attach the distal head 26 to the catheter body 20. The distal head 26 may be formed of any suitable rigid material such as metal or plastic. In devices wherein the distal head is formed of plastic, the surrounding plastic catheter body 20 may be thoroughly welded, heat sealed or solvent welded to the plastic distal head 26, in accordance with the types of plastics employed.

In the alternative to the use of adhesives, various mechanical or frictional connectors, such as screw threads, lugs or other surface modifications formed on the proximal portion 30 of the distal head 26, may be utilized to hold the distal head 26 in a fixed position relative to the catheter body 20. In such embodiments, corresponding grooves, detents or surface modifications may also be formed in the surrounding inner wall of the catheter body 20 so as to cooperate with any such threads, lugs or other surface modifications formed on the opposing surface of the distal head 26. Such threads, lugs or other surface modifications will be configured and constructed so as to mechanically or frictionally hold the distal head 26 in fixed position relative to the catheter body 20.

The distal head 26 is preferably formed of radiodense material so as to be easily discernable by radiographic means. Accordingly, the distal head 26 may preferably be formed of metal or, alternatively, may be formed of plastic, ceramic or rubber materials, optionally having one or more radiodense markers affixed thereto or formed therein. For example, the distal head 26 may be molded of plastic such as acrylonitrile-butadiene-styrene (ABS) and one or more metallic foil strips or other radio opaque markers may be affixed to such plastic distal head 26 in order to impart sufficient radiodensity to permit the distal head 26 to be readily located by radiographic means. Additionally, in embodiments wherein the distal head 26 is formed of molded plastic or other non-metallic material, a quantity of radiodense filler such as powdered bismuth or $BaSO_4$ may be disposed within the plastic or other non-metallic material of which the distal head 26 is formed so as to impart enhanced radiodensity to the distal head 26.

An optional guidewire passage aperture 40 may extend longitudinally through the distal head 26. Such guidewire passage aperture 40 may be formed through the distal head at a location inboard of the catheter body 20 such that a guidewire 42 may be advanced through a lumen 22 of the catheter body and through guidewire passage aperture 40. Such embodiments of the ultrasound catheter 10 wherein the guidewire 42 passes through a lumen formed within the catheter body 20 and out of the catheter passage aperture 40 constitute an "over-the-wire" embodiment of the invention.

Alternatively, the distal head 26a may be formed such that a portion of the distal head extends laterally outboard of the outer surface of the catheter body 20a and the guidewire passage aperture 40a may be, likewise, positioned outboard of the outer surface of the catheter body 20a thereby forming a guidewire alongside the catheter body 20a and through the guidewire passage aperture 40a. Such embodiments of the invention wherein the guidewire 42a is passed outboard of the outer surface of the catheter body 20a and through catheter passage aperture 40a are referred to sometimes herein as "monorail" embodiments.

In addition to the over-the-wire embodiment (FIG. 2) and the "monorail" embodiment (FIG. 4) the ultrasound catheter of the present invention may also be formed in embodiments which constitute combinations or hybrids of such over-the-wire and monorail embodiments, as shown in FIGS. 5, 5a and 6. Specifically, such embodiments of the invention comprise an ultrasound catheter having a guidewire passage lumen formed through a distal portion of the catheter body only, with a guidewire entry/re-entry aperture 160 being formed through a sidewall of the catheter to permit passage of the guidewire 42 from the distal guidewire lumen of the catheter to a position outside the catheter body.

As shown in FIGS. 5, 5a and 6, the catheter body 20b may be provided with a distal guidewire passage tube 156 positioned within the inner bore or lumen 22b of the catheter body 20b and extending from a guidewire re-entry aperture 160 to the guidewire passage aperture 40b formed in the distal head 26b of the device. As such, the proximal end of a pre-inserted guidewire may be inserted into the distal end of the catheter body 20b through guidewire passage aperture 40b and subsequently advanced in a proximal direction through the guidewire lumen 158 to a point where the proximal end of the guidewire 42 emerges out of guidewire entry/re-entry aperture 160. After emerging from guidewire entry/re-entry aperture 160, the proximal portion of the guidewire 42 may extend and/or reside adjacent the outer surface of the proximal portion of the catheter body 20b as shown. The catheter body 20b and the guidewire 42 may then be distally and/or proximally repositioned, relative to one another, during the procedure. Also, if desired, the guidewire 42 may be fully withdrawn and extracted by pulling the guidewire in a proximal direction such that the distal tip of the guidewire is pulled out of the guidewire entry/re-entry aperture 160 and the guidewire 42 is subsequently fully withdrawn out of the body, leaving only the ultrasound catheter in place.

Another alternative configuration and construction of the distal head 26 is shown in the embodiments of FIGS. 5, 5a, 6, 6a and 6b. In such embodiments, the distal head 26b, 26c is secured to the distal end of the catheter body 20b, 20c by way of an annular ring member 150 and a quantity of adhesive ADH. As specifically shown in the views of FIG. 6, 6a and 6b, this embodiment of the distal head 26b comprises a distal portion 28b and a reduced diameter proximal portion 30b which is insertable into the distal end of the lumen 22b of the catheter body 20b. The distal portion 28b of the distal head 26b has a grooved detent or annular shoulder 148 formed therein. The proximal portion 30b of the distal head 26b is inserted into the distal end of the lumen 20b of the catheter body and may be secured thereto by way of a quantity of adhesive. An annular ring member 150 is then passed in a proximal direction over the catheter body 20b and advanced to a point where the annular ring member 150 abuts against shoulder 148. A quantity of adhesive ADH is then applied to secure the annular ring member 150 around the distal tip of the catheter body 20b and the part of the distal portion 28b of the distal head 26b. The adhesive ADH may be tapered or smoothed to form a constant angular transition from the distal portion 28b of the distal head 26b to the outer surface of the catheter body 20b as shown. The distal head 26b and annular ring member 150 may be formed of any suitable rigid material such as metal or plastic. In embodiments where metal materials are employed, metal bonding or metal welding may be utilized as an alternative to or in addition to the use of adhesives for bonding the assembly to the distal end of the catheter body 20b. In embodiments wherein the distal head 26b and annular ring member 150 are formed of plastic, thermal welding, heat fusing or solvent welding techniques may be used as an alternative or in addition to the use of adhesives for such purpose.

In the embodiment of the distal head shown in FIGS. 5–6, it is preferable that the outer diameter of the annular ring member 150 be approximately the same as the largest outer diameter of the extreme distal portion 28b of the distal head 26b such that a smooth transition is formed from the distal head 26b to the outer surface of the catheter body 20b.

Optionally, one or more fluid outflow aperture(s) 50 are formed at or near the distal end of the catheter body 20 to permit fluid to flow out of a lumen 22 of the catheter 10. The provision of such fluid outflow aperture(s) 50 near the distal end of the catheter 10 facilitates continual or intermittent passage of coolant liquid into the proximal end of the lumen 22, distally through the lumen 22, and out of fluid outflow aperture(s) 50. Preferably, the lumen 22 of the catheter 10 into which the fluid outflow aperture(s) communicates will be the same lumen wherein the ultrasound transmission member 24 is located such that coolant liquid may be infused into the proximal end of such lumen 22, distally therethrough and out of fluid outflow aperture(s) 50 in a manner that will bathe and cool the body of the ultrasound transmission member 24, thereby preventing the ultrasound transmission member 24 from overheating during use.

In addition to, or in the alternative to, the optional fluid outflow aperture(s) 50 formed in the catheter body 20, one or more fluid outflow aperture(s) 51 may be formed through the distal head 26 to permit fluid to flow directly out of the distal end of the catheter 10. In embodiments having a guidewire aperture 40 formed through the distal head 26, such guidewire aperture may be slightly larger than the outer diameter of the guidewire 42 to be passed therethrough so as to permit fluid to be infused through the guidewire lumen and to pass out of the guidewire aperture 40, even when a guidewire 42 is extending therethrough. Thus, the guidewire aperture 40 may, in some embodiments, preclude the necessity for and/or perform the function of a separate dedicated fluid outflow aperture 51 extending through the distal head 26.

Optionally, one or more separate lumens having separate outflow apertures formed at or near the distal tip of the catheter may be formed for infusion of oxygenated perfusate, medicaments or other fluids into the blood vessel or other anatomical structure in which the catheter is positioned.

Various types and designs of proximal end connector apparatus 12 may be positioned on the proximal end of the catheter body to facilitate operative connection of the ultrasound transmission member 24 to an ultrasound transducer 14 and ultrasound generation device 16. Examples of embodiments of such proximal end connector apparatus 12 are shown in FIGS. 7-10. FIG. 7 shows a relatively simple proximal end connector apparatus 12a configured for use in connection with catheters which do not incorporate internal guidewire passage lumens. FIG. 8 shows a more complex proximal end connector 12b configured for use in connection with catheters having internal guidewire passage lumens.

The embodiment of the proximal end connector 12a shown in FIG. 7 comprises a rear portion 92 and a mid-portion 90. A gripping member 96 formed on the proximal end of the mid-portion 90 operates to attach the proximal end connector 12a to the proximal end of the catheter 20. The mid-portion 90 comprises an elongate tubular body 80 having a tubular fluid infusion sidearm 82 extending outwardly therefrom to permit infusion of coolant fluid or other liquid into the inner lumen 81 of the proximal end connector 12a.

The more complex embodiment of the proximal end connector 12b shown in FIG. 8 comprises the same rear portion 92 and mid-portion 90 as the simpler embodiment 12a shown in FIG. 7. However, the more complex embodiment 12b of FIG. 8 further comprises a frontal portion 88 which is configured and constructed to facilitate insertion and/or extraction of a guidewire 42 through a lumen or passageway formed internally within the catheter 20.

In both embodiments shown, the proximal end connector apparatus 12 comprises an elongate rigid body 80 having a hollow bore 81 extending longitudinally therethrough. In the embodiment shown, the elongate body of the proximal end connector 12 is actually constructed of a frontal portion 88, a mid-portion 90 and a rear portion 92. The frontal portion 88 of the elongate body 80 is firmly connected to the proximal end of the catheter body 20 by way of a threaded gripping member 94. A sleeve 21 having an annular flange 23 formed on the proximal end thereof is positioned on the proximal end of the catheter body 20 to engage gripping member 94 as shown. The proximal end of the frontal portion 88 is connected to the distal end of the mid-portion 90 of the elongate body 80 by way of a second gripping member 96. Accordingly, to facilitate such construction, threads 98, 100 are formed on the opposite ends of the frontal portion 88 of the elongate body 80.

Threads 102 are also formed on the proximal end of the mid-portion 90 of the elongate body 80 such that the mid-portion 90 may be threadably mounted within a correspondingly threaded bore formed in the distal end of the rear portion 92 of the elongate body 80. An O-ring 104 is positioned at the bottom of the threaded bore formed in the distal end of the rear portion 92 such that, when the rear portion 92 is tightened over the threads 102 of the mid-portion 90, the proximal end 108 of the mid-portion 90 will abut against and compress O-ring 104 against ledge 105, thereby causing O-ring 104 to exert inward pressure against tube 110. Tube 110 extends longitudinally through the hollow bore 81 within the rear portion 92 of the proximal connector apparatus 12. The ultrasound transmission member 24 or wave guide extends longitudinally through the entire catheter body 20 and through the proximal end connector 12. The ultrasound transmission member 24 or wave guide is inserted into and engaged by threaded proximal connector 112. Threaded proximal connector 112 is positioned within a cylindrical recess 114 formed in the proximal end of the proximal connector apparatus 12. A suitable ultrasound transducer 14 may be screwed onto and threadably connected to the threaded proximal connector 112 to accomplish passage of ultrasonic energy through the ultrasound transmission member 24 in a distal direction to the distal head 26 of the device.

The extreme proximal end of the proximal connector 12 is provided with a sonic connector assembly or apparatus configured to effect operative attachment of the proximal end of the ultrasound transmission member 24 to the horn of an ultrasound transducer 14. The sonic connector assembly or apparatus is preferably configured and constructed to permit passage of ultrasound energy through the ultrasound transmission member or wave guide 24 with minimal lateral side-to-side movement of the ultrasound transmission member 24 while, at the same time, permitting unrestricted longitudinal forward/backward vibration or movement of the ultrasound transmission member 24.

In one embodiment of the sonic connector shown in FIG. 10, a distal portion of the body of the threaded proximal connector 112 is configured to receive therein a compressible gripping ferrule 116. Compressible gripping ferrule 116 has a small central aperture formed therethrough through which the ultrasound transmission member 24 passes, as shown. A frontal member 118 is threadably tightened within the frontal portion of the body of proximal connector member 112 so as to compress gripping ferrule 116, thereby causing gripping ferrule 116 to firmly grip and hold the ultrasound transmission member 24 in place within the body of the proximal connector member 112. The proximal connector member 112 may then be compressed or crimped inwardly so as to be additionally crimp connected or crimp fit to the proximal end of the ultrasound transmission member 24, thereby providing further gripping and attachment of the sonic connector assembly to the proximal end of the ultrasound transmission member. A series of threads are formed on the outer surface of the proximal connector member 112 to permit the distal end of an ultrasound transducer horn to be threadably screwed onto and releasably attached to the sonic connector assembly. Thus, the frontal member 118, gripping ferrule 116, and proximal connector member 112 combine to form a sonic connector assembly to which the horn of an ultrasound transducer may be attached and through which the ultrasonic energy may be transmitted into the ultrasound transmission member, with the gripping ferrule 116 acting to dampen transverse movement of the ultrasound transmission member 24.

In a second embodiment of the sonic connector, which is shown in FIGS. 11 and 12, a frontal member 218 is positionable on the ultrasound transmission member 24, and has a stem 220 with threads 222 provided thereon for threadable engagement with threads 221 provided in an opening of a proximal connector 212. A plurality of compressible plugs 224 are configured to fit within the opening of the proximal connector 212 perpendicular to the axis of the ultrasound transmission member 24. In the preferred embodiment, four compressible plugs 224 are provided, but it will be appreciated by those skilled in the art that any number of compressible plugs 224 may be distributed about the circumference of the ultrasound transmission member 24. The proximal connector 212 is also positionable on the ultrasound transmission member 24 and also has a stem 214 with threads 216 provided thereon for threadable engagement with threads 217 provided on a cavity 226 of a horn 228 of the ultrasound transducer 14. Again, a plurality of compressible plugs 224 are configured to fit within the cavity 226 of the ultrasound transducer horn 228 perpendicular to the axis of the ultrasound transmission member 24. The proximal-most end of the ultrasound transmission member 24 terminates at the promixal-most end of the stem 214 within the cavity 226. The stem 214 and the ultrasound transmission member 24 may be crimped as shown at 230 to provide a more stable connection between the sonic connector assembly and the ultrasound transmission member 24. The frontal member 218 and the proximal connector 212 are preferably made from stainless steel.

The compressible plugs 224 are preferably disposed along the threads 216, 217, 221 and 222 so that when the frontal member 218 is threadably screwed onto the proximal connector 212 and the proximal connector 212 is in turn threadably screwed onto the ultrasound transducer horn 228, the threads 216, 217, 221 and 222 exert an inward force against the plugs 224 provided thereat, thereby forcing the plugs 224 against the ultrasound transmission member 24 to provide a firm grip to minimize transverse movement of the ultrasound transmission member 24. The compressible plugs 224 are preferably made from any compliant material such as plastic, nylon, teflon, ABS, polypropylene, polyolefins, natural and synthetic rubbers and ethylene vinyl acetate (EVA). The compliance of the plugs 224 also secures the threaded connection between the frontal member 218 and the proximal connector 212 so that this connection does not become loosened, which would otherwise cause the ultrasound transmission member 24 to become disengaged. It will be appreciated by those skilled in the art that the plugs 224 may be provided at the threads 221 and 222 only, or at the threads 216 and 217 only, at both sets of threads 216 and 217 and 221 and 222, or elsewhere along the stems 214 and 220.

In a third embodiment of the sonic connector, which is shown in FIG. 13, a gripping ferrule 116 is positioned between the threaded connection between the frontal member 218 and the proximal connector 212. A plurality of compressible plugs 224 are positioned between the threaded connection between the proximal connector 212 and the transducer horn 228. Thus, the embodiment of FIG. 13 utilizes both the gripping ferrule and the compressible plugs to achieve the damping of transverse movement by the ultrasound transmission member 24, and to secure the ultrasound transmission member 24 to the sonic connector.

Figure 14:
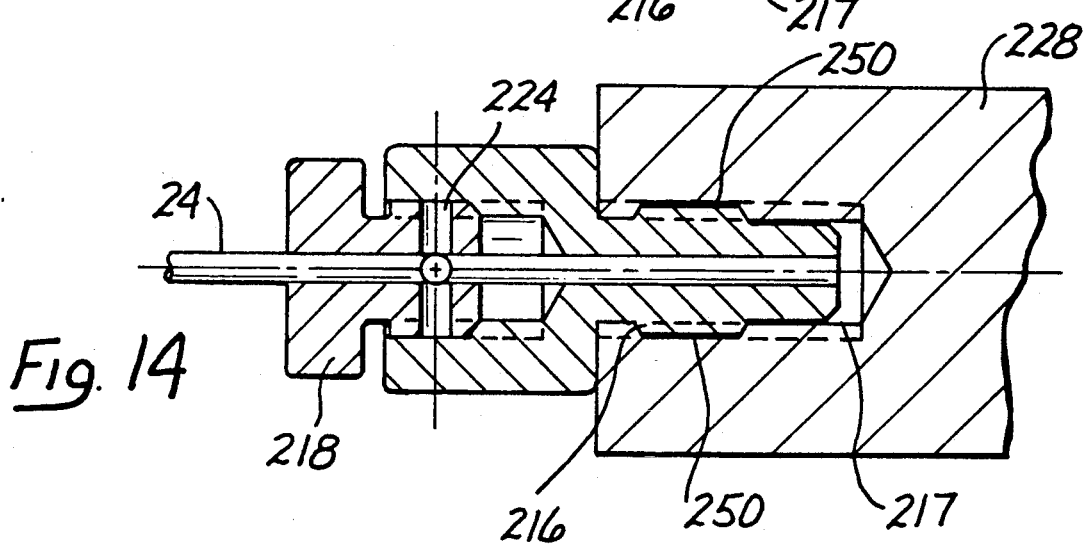
FIG. 14 is an enlarged perspective view of a fourth embodiment of a sonic connector positioned within the proximal end connector assembly of FIG. 10.
Figure 15:
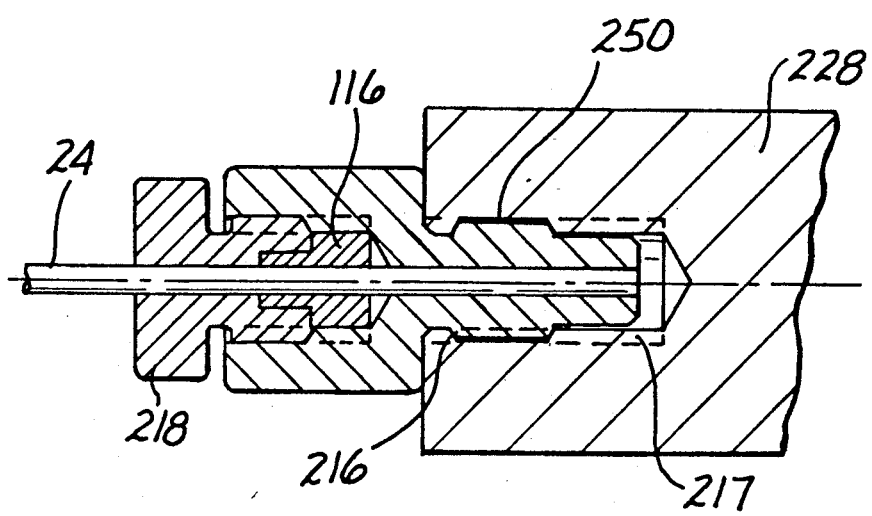
FIG. 15 is an enlarged perspective view of a fifth embodiment of a sonic connector positioned within the proximal end connector assembly of FIG. 10.

Alternatively, a polymeric coating may be applied to the threads 216, 217, 221 and 222. The coating creates friction which functions to secure the threaded connections and prevent the threaded connections from becoming loose. This polymeric coating may be made by PVC dispersions using a solvent release approach, or by thermal application of various thermoplastics such as polyethelene, EVA, and nylon, among others. It will be appreciated by those skilled in the art that the polymeric coating may be applied independent of the compressible plugs 224, or in conjunction with the compressible plugs 224. The polymeric coating may also be applied to the threaded regions of the first embodiment of the sonic connector assembly described in connection with FIG. 10. Alternatively, the polymeric coating may also be applied between the threaded connection between the proximal connector 212 and the transducer horn 228, with compressible plugs 224 or a gripping ferrule 116 provided between the threaded connection between the frontal member 218 and the proximal connector 212. For example, the embodiment of FIG. 14 has a polymeric coating 250 provided between the transducer horn 228 and the proximal connector 212, with compressible plugs 224 provided between the frontal member 218 and the proximal connector 212. Similarly, the embodiment of FIG. 15 has a polymeric coating 250 provided between the transducer horn 228 and the proximal connector 212, with a gripping ferrule 116 provided between the frontal member 218 and the proximal connector 212.

The elongate tube 110 which extends through the rear portion 92 of the proximal connector apparatus 12 is specifically sized such that the lumen 120 of the tube 110 is large enough to permit the ultrasound transmission member 142 to pass therethrough with a small amount of space remaining between the outer surface of the ultrasound transmission member 24 and the inner luminal surface of the tube 110.

A fluid inlet sidearm 82 is formed on the rigid body 80 of the proximal end connector apparatus 12. Such fluid inlet sidearm 82 has a hollow bore 122 which extends therethrough and is in fluid communication with the longitudinal bore 81 of the proximal end connector 12.

Thus, pressurized fluid, such as a coolant liquid, may be infused through sidearm 82, through bore 81 and through the lumen 22 of the catheter body 20 to a point where such liquid flows out of fluid outflow apertures 50. The temperature and flow rate of such coolant liquid may be specifically controlled to maintain the temperature of the ultrasound transmission member 24 at a desired temperature within its optimal working range. In particular, in embodiments of the invention wherein the ultrasound transmission member 24 is formed of a metal alloy which exhibits optimal physical properties (e.g. super elasticity) within a specific range of temperatures, the temperature and flow rate of coolant liquid infused through fluid infusion sidearm 82 may be specifically controlled to maintain the temperature of the ultrasound transmission member within the range of temperatures at which it demonstrates its most desirable physical properties. For example, in embodiments of the invention wherein the ultrasound transmission member 24 is formed of a shape memory alloy which exhibits super elasticity when in its martensite state, but which loses super elasticity as it transitions to an austenite state, it will be desirable to adjust the temperature and flow rate of the coolant liquid infused through fluid infusion sidearm 82 so as to maintain the shape memory alloy of the ultrasound transmission member 24 within a temperature range at which the alloy will remain in its martensite state and will not transition to an austenite state. The temperature at which such shape memory alloys transition from a martensite state to an austenite state is known as the "martensite transition temperature" ($M_s$) of the material. Thus, in these embodiments, the fluid infused through sidearm 82 will be at such temperature, and will be infused at such rate, as to maintain the shape memory alloy of the ultrasound transmission member 24 below its martensite transition temperature ($M_s$).

A guidewire insertion sidearm 84 may also be formed on the elongate body 80 of the proximal end connector apparatus 12. Such guidewire passage sidearm 84 has a hollow lumen 130 extending therethrough and communicating with the longitudinal bore 81 of the proximal end connector 12. A guidewire gripping/sealing apparatus 132 may be mounted on guidewire passage sidearm 84 to grasp and hold the guidewire 42 in fixed longitudinal position relative to the catheter 10 and to provide a seal to prevent backflow of blood through the catheter 10. Examples of guidewire gripping/sealing apparatus 132 which may be utilized in this application include those which are which are available commercially as Product Nos. 1905017A and 1905014A from Medical Disposables International, West Conshocken, Pa. Such commercially available guidewire gripping-/valving apparatus 132 may be modified by inserting a segment of plastic tubing 134 into the bore of such device to permit such device 132 to grip and seal against a guidewire 42 which is smaller in diameter than the existing diameter of the seal provided in such commercially available MDI sealing/valving apparatus 132. Other sealing/valving apparatus may also be employed.

Additionally, in the embodiment shown in FIG. 9, an angled guidewire diverter tube 140 is positioned within the bore 130 of the guidewire passage sidearm 84 and a portion of the longitudinal bore 81 of the body 80 of the proximal end connector apparatus 12. Such guidewire diverter tube 140 comprises an obtuse angular bend B having an aperture 142 formed at the outer apex of such angular bend B. The aperture 142 is sufficiently large to permit the ultrasound transmission member 24 to pass longitudinally therethrough without damping or interference from the body of the tube 140. Also, the aperture 142 is sufficiently large to allow irrigation/coolant liquid to flow therethrough when the ultrasound transmission member 24 is positioned within the aperture 142.

The guidewire diverter tube 140 is configured and constructed such that, as the proximal end of guidewire 42 is advanced in a proximal direction through the longitudinal bore 81 of the elongate body 80 of the proximal end connector 12, it will impinge against the wall of guidewire diverter tube 140 and will thus be diverted outwardly through the guidewire passage sidearm 84.

Although the invention has been described herein with specific reference to presently preferred embodiments thereof, it will be appreciated by those skilled in the art that various additions, modifications, deletions and alterations may be made to such preferred embodiments without departing from the spirit and scope of the invention. Accordingly, it is intended that all reasonably foreseeable additions, deletions, alterations and modifications be included within the scope of the invention as defined in the following claims.

What is claimed is:

1. An ultrasonic catheter for removing obstructions from tubular anatomical structures such as blood vessels, said ultrasonic catheter comprising:
    an elongated flexible catheter body having a proximal end, a distal end and at least one lumen extending longitudinally therethrough;
    an ultrasound transmission member extending longitudinally through said lumen of said catheter, said ultrasound transmission member having a proximal end connectable to a separate ultrasound generating device and a distal end terminating adjacent the distal end of said catheter body;
    a sonic connector assembly being positioned on the proximal end of said ultrasound transmission member to facilitate connection of said ultrasound transmission member to a separate ultrasound transducer, said sonic connector assembly comprising;
    (i) a frontal member positionable on said ultrasound transmission member and having a threaded region formed thereon;
    (ii) a proximal member positionable on said ultrasound transmission member and having a first threaded region formed thereon and rotatably engageable with the threaded region of said frontal member component, said proximal member further including a stem provided with a series of threads thereby forming a second threaded region, said stem configured to receive a correspondingly threaded bore of the horn of a separate ultrasound transducer;
    (iii) first means positionable between said proximal member and said bore of said transducer horn;
    (iv) second means positionable between said frontal member and said proximal member;
    (v) said first means being sized and configured relative to said proximal member and said transducer horn, and said second means being sized, configured and constructed relative to said frontal member and said proximal member, such that said first and second means will become inwardly compressed against said ultrasound transmission member when said frontal member component and said proximal member are connected to one another and when said proximal member and said bore of said transducer horn are connected to one another by rotatable threaded connection.

2. The ultrasonic catheter of claim 1 wherein said sonic connector assembly is positioned on the extreme proximal end of said ultrasound transmission member with the proximal end of said ultrasound transmission member being coterminous with the proximal-most extent of said proximal member of said sonic connector assembly.

3. The ultrasonic catheter of claim 1 wherein said proximal member is further affixed to said ultrasound transmission member to accomplish additional crimp connection of said sonic connector assembly to said ultrasound transmission member.

4. The ultrasonic catheter of claim 1 wherein said threaded region of said frontal member, said first threaded region of said proximal member, said second threaded region of said proximal member, and said threaded bore of said transducer horn are coated with a polymeric coating.

5. The ultrasonic catheter of claim 1 wherein said first means comprises a compressible gripping ferrule.

6. The ultrasonic catheter of claim 5 wherein said second means comprises a plurality of compressible plugs.

7. The ultrasonic catheter of claim 1 wherein said first means comprises a plurality of compressible plugs.

8. The ultrasonic catheter of claim 7 wherein said second means comprises a plurality of compressible plugs.

9. The ultrasonic catheter of claim 5 wherein said second means comprises a gripping ferrule.

10. An ultrasonic catheter for removing obstructions from tubular anatomical structures such as blood vessels, said ultrasonic catheter comprising:
    an elongated flexible catheter body having a proximal end, a distal end and at least one lumen extending longitudinally therethrough;
    an ultrasound transmission member extending longitudinally through said lumen of said catheter, said ultrasound transmission member having a proximal end connectable to a separate ultrasound generating device and a distal end terminating adjacent the distal end of said catheter body;
    a sonic connector assembly being positioned on the proximal end of said ultrasound transmission member to facilitate connection of said ultrasound transmission member to a separate ultrasound transducer, said sonic connector assembly comprising;

(i) a frontal member positionable on said ultrasound transmission member and having a threaded region formed thereon;

(ii) a proximal member positionable on said ultrasound transmission member and having a first threaded region formed thereon and rotatably engageable with the threaded region of said frontal member component with a said proximal member further including a stem provided with a series of threads thereby forming a second threaded region, said stem configured to receive a correspondingly threaded bore of the horn of a separate ultrasound transducer;

(iii) a plurality of compressible plugs positionable between said proximal member and said bore of said transducer horn;

(iv) a compressible gripping ferrule positionable between said frontal member and said proximal member;

(v) said plurality of compressible plugs being sized and configured relative to said proximal member and said transducer horn, and said gripping ferrule being sized, configured and constructed relative to said frontal member and said proximal member, such that said gripping ferrule and said plurality of plugs will become inwardly compressed against said ultrasound transmission member when said frontal member component and said proximal member are connected to one another and when said proximal member and said bore of said transducer horn are connected to one another by rotatable threaded connection.

11. The ultrasonic catheter of claim 10 wherein said sonic connector assembly is positioned on the extreme proximal end of said ultrasound transmission member with the proximal end of said ultrasound transmission member being coterminous with the proximal-most extent of said proximal member of said sonic connector assembly.

12. The ultrasonic catheter of claim 10 wherein said proximal member is further affixed to said ultrasound transmission member to accomplish additional crimp connection of said sonic connector assembly to said ultrasound transmission member.

13. The ultrasonic catheter of claim 10 wherein said plurality of plugs are positioned on said second threaded region of said proximal member.

14. The ultrasonic catheter of claim 10 wherein said threaded region of said frontal member, said first threaded region of said proximal member, said second threaded region of said proximal member, and said threaded bore of said transducer horn are coated with a polymeric coating.

* * * * *